United States Patent [19]
Hurd et al.

[11] Patent Number: 6,074,829
[45] Date of Patent: Jun. 13, 2000

[54] RELATING TO ASSAY SYSTEMS

[75] Inventors: Douglas Hurd; Rachel Alison Fallon, both of Oxford; Michael White, Warrington; Nicholas Jones, Hutton, all of United Kingdom

[73] Assignee: Amersham International PLC, Buckinghamshire, United Kingdom

[21] Appl. No.: 09/091,348

[22] PCT Filed: Dec. 20, 1996

[86] PCT No.: PCT/GB96/03172

§ 371 Date: Aug. 25, 1998

§ 102(e) Date: Aug. 25, 1998

[87] PCT Pub. No.: WO97/23609

PCT Pub. Date: Jul. 3, 1997

[30] Foreign Application Priority Data

Dec. 21, 1995 [EP] European Pat. Off. .............. 95309340

[51] Int. Cl.[7] .............................. C12Q 1/68; C12N 15/63
[52] U.S. Cl. ............................................ 435/6; 435/320.1
[58] Field of Search ........................ 435/6, 254.2, 254.21, 435/320.1

[56] References Cited

FOREIGN PATENT DOCUMENTS

| 94/10300 | 5/1994 | WIPO . |
| 95/20652 | 8/1995 | WIPO . |

OTHER PUBLICATIONS

P. Bartel et al., "Elimination of false positives that arise in using the two–hybrid system", Biotechniques, vol. 14, No. 6, pp. 920–922, (1993).

B. Le Douarin et al., "A new version of the two–hybrid assay for detection of protein–protein interactions", Nucleic Acids Research, vol. 23, No. 5, pp. 876–878, (1995).

J. Harper et al., "The p21 Cdk–interacting protein Cip 1 is a potent inhibitor of G1 cyclin–dependent kinase", Cell, vol. 75, pp. 805–816, Nov. 19, 1993.

J. Luban et al. "The yeast two–hybrid system for studying protein–protein interactions", Current Opinion in Biotechnology, vol. 6, No. 1, pp. 59–64, (1995).

C. Bendixen et al., "A yeast mating–selection scheme for detection of protein–protein interactions", Nucleic Acids Research, vol. 22, No. 9, pp. 1778–1779, (1994).

T. Wilson et al., "A genetic method for defining DNA–binding domains: application to the nuclear receptor NGFI–B", Proc. Natl. Acad. Sci., vol. 90, pp. 9186–9190, Oct. 1993.

S. Dalton et al., "Characterization of SAP–1, a protein recruited by serum response factor to the c–fos serum response element", Cell, vol. 68, pp. 597–612, Feb. 7, 1992.

U. Yavuzer et al., "pWITCH: a versatile two–hybrid assay vector for the production of epitope/activation domain–tagged proteins both in vitro and in yeast", Gene, vol. 165, pp. 93–96, Nov. 1995.

*Primary Examiner*—Robert A. Schwartzman
*Attorney, Agent, or Firm*—Wenderoth, Lind & Ponack, L.L.P.

[57] ABSTRACT

A method for detecting an interaction between two proteins while eliminating false positive interactions, the method being particularly useful for application in the two-hybrid system and for the screening of libraries of unknown proteins. In a two-hybrid system employing the method, two different repoter genes having different promoters and two different DNA-binding domains which specifically bind to those promoters, are used.

11 Claims, 1 Drawing Sheet

SEQUENCE LISTING

```
<160> NUMBER OF SEQ ID NOS: 14

<210> SEQ ID NO 1
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 1
gcgcgcgagc tcgagcaata aagattctac aatactagc                         39

<210> SEQ ID NO 2
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 2
ggcccggaat tcgtcgacag tcaagatctt atagtttttt ctccttgacg tt          52

<210> SEQ ID NO 3
<211> LENGTH: 34
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 3
gcgcgcggat ccaaaatgac agagcagaaa gccc                              34
```

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 4
ggccgcgaat tccggtgtca ctacataaga ac                                  32

<210> SEQ ID NO 5
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
tcgactgctg tatataaaac cagtggttat atgtacagta cg                       42

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
tcgacgtact gtacatataa ccactggttt tatatacagc ag                       42

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 7
ggctcgaggt cgacgaagta cggattagaa gcc                                 33

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 8
ggctcgagtt cggagcagtg cggcg                                          25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 9
cgtcctttga gacagcattc                                                20

<210> SEQ ID NO 10

```
<211> LENGTH: 22
<212> TYPE: DNA
<213> ORGANISM: Artificial Sequence
<220> FEATURE:
<223> OTHER INFORMATION: Description of Artificial Sequence: Synthetic
      DNA Primer

<400> SEQUENCE: 10
gttacatggc caagattgaa ac                                              22

<210> SEQ ID NO 11
<211> LENGTH: 12
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
aattccagct gg                                                         12

<210> SEQ ID NO 12
<211> LENGTH: 12
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
gatcccagct gg                                                         12

<210> SEQ ID NO 13
<211> LENGTH: 45
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
tatgaacctg caggaaagaa ttctggatcc atgcggccgc gtgca                     45

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
cgcggccgca tggatccaga attctttcct gcaggttca                            39
```

RELATING TO ASSAY SYSTEMS

The invention is concerned with improvements in methods for detecting protein-protein interactions, more specifically with the reduction or elimination of false positives. The invention relates in particular to improvements to two-hybrid or interaction trap systems for selecting for interacting proteins in living cells. The invention also includes modifications to hybrid constructs and to vectors and yeast strains expressing such constructs.

BACKGROUND OF THE INVENTION

In the two-hybrid system of Fields and Song(1) described in U.S. Pat. No. 5,283,173 two chimeric genes which encode hybrid proteins are used to test the interaction between a known protein and protein of interest. The first chimeric gene codes for a known protein, often called the bait protein, fused to a DNA-binding domain. The second chimeric gene codes for a protein of interest fused to the transcriptional activation domain. Additionally, the protein of interest may not be known and could be derived for example from a cDNA library. In a suitable host cell such as yeast, if the protein of interest and the bait protein do interact they bring into proximity the DNA-binding and transcriptional activation domains. This proximity is sufficient to cause transcription of a marker gene placed under the control of a promoter containing a binding site for the DNA-binding domain.

Yeast genetic systems have also been used in methods for defining DNA-binding domains of proteins. One such method (2) uses a chimeric protein containing a transcriptional activation domain together with two DNA-binding domains, each capable of binding to a different reporter gene. One of the DNA-binding domains is mutated to analyse its DNA-binding properties.

In the two-hybrid system, once a specific cDNA-encoded protein or known protein of interest has been shown to give rise to activation of the marker gene, it is important to show that this is indeed due to an interaction between the bait protein and the protein of interest and not due to a "false positive" interaction (3). At least four classes of false positives may occur in two-hybrid systems where a protein of interest, which may be encoded by a cDNA library, is fused to the activation domain:

1. A DNA-binding domain might be cloned into the activator hybrid which would activate transcription independent of the DNA-binding hybrid, by binding:
   a) to the DNA binding site or
   b) to the basal portion of the promoter;
2. Protein in the activator hybrid might bind to the DNA-binding domain of the bait hybrid;
3. Protein in the activator hybrid might bind to the novel junction formed between the protein and an epitope tag or tags encoded by the bait hybrid vector, or to the epitope tag(s) itself;
4. Protein in the bait hybrid might bind to the novel junction formed between the protein of interest and an eptiope tag or tags encoded by the activator hybrid vector.

A number of strategies have been previously described which remove some of the above classes of false positives (3). Three such strategies are as follows:
1. The use of two marker genes (3). One of these genes usually expresses a selectable marker (eg. HIS3) and the other one a measurable marker activity (eg. lacZ) and the reporter gene promoters are usually different. This allows the removal of those proteins in the first class of false positive where a non-specific interaction occurs between the protein and the promoter of the marker gene, since non-specific interaction with both of the marker gene promoters is less likely to occur.
2. The use of curing to remove the bait hybrid protein (4). This strategy removes the bait hybrid plasmid, so that only the activator hybrid expressing the protein of interest is present in the cell. If the marker gene expression remains high, then this shows that the activation is due to spurious promoter activation by the protein of interest hybrid protein, rather than via binding through the bait protein hybrid.
3. The use of an unrelated bait protein (3). This is to ensure that the protein interacts with the bait protein of interest and no other part of the bait hybrid protein.

A review by Allen et al 1995 (5) describes strategies for the removal of false positives. One of these, elaborated on in Harper et al 1993 (6), involves curing out the bait hybrid and using unrelated bait proteins fused to the DNA-binding domain of the original bait protein, to detect false positives.

Another strategy is described by Le Douarin et al 1995 (7). When an apparent positive interaction is detected, the bait hybrid protein is removed by curing and a bait hybrid containing a different DNA-binding domain is introduced. False positives are indicated if there is activation of a reporter construct to which the different DNA-binding domain binds.

Strategies which have previously been applied to the problem of false positives in two-hybrid systems generally remove only some of the above classes of false positives. Known strategies can in principle be used consecutively to remove all false positives, but this will entail lengthy and complicated procedures. The previously used strategies which do remove several classes of false positives require lengthy and labour intensive screening steps after the initial screen. No strategy has been devised which would be able to remove all of these false positives at the initial screening step. Furthermore, there has so far been no strategy for removing false positives in the screening of two libraries against each other in a search for pairs of interacting proteins. Clearly, there is a need for methods of effectively eliminating false positives in these systems.

SUMMARY OF THE INVENTION

The present invention aims to provide methods for detecting interactions between proteins, which avoid some or all of the problems with known methods. In particular, the invention aims to overcome difficulties with the present two-hybrid methods, such as the need for curing of (removing plasmids from) transformed strains, multiple plasmid rescues and retransformations or significant downstream protein analysis before false positives are identified. The invention also aims to make it feasible to screen two libraries against each other to identify interacting proteins.

The present invention therefore provides a method for detecting an interaction between a first test protein and a second test protein, which method comprises:
   a) providing a host cell;
   b) providing a first chimeric gene that is capable of being expressed in the host cell, the first chimeric gene comprising a DNA sequence that encodes a first hybrid protein, the first hybrid protein comprising:
      (i) a first test protein that is to be tested for interaction with a second test protein; and
      (ii) a first detection domain;
   c) providing a second chimeric gene that is capable of being expressed in the host cell, the second chimeric gene comprising a DNA sequence that encodes a second hybrid protein, the second hybrid protein comprising:
  (i) a second test protein that is to be tested for interaction with the first test protein; and
  (ii) a second detection domain;
d) providing a control chimeric gene that is capable of being expressed in the host cell, the control chimeric gene comprising a DNA sequence that encodes a control hybrid protein, the control hybrid protein comprising:
  (i) the first test protein; and
  (ii) a control detection domain;
  wherein when the first detection domain and the second detection domain are brought into proximity to one another by an interaction between the first and second hybrid proteins, a first detectable signal is produced, and when the second detection domain and the control detection domain are brought into proximity to one another by an interaction between the second hybrid protein and the control hybrid protein a second detectable signal is produced which is distinguishable from the first detectable signal;
e) introducing the first chimeric gene and the second chimeric gene into the host cell and subjecting the host cell to conditions under which the first and second hybrid proteins are expressed in sufficient quantity for the first detectable signal to be produced;
f) introducing the control chimeric gene into the host cell in the presence of the first and second chimeric genes and subjecting the host cell to conditions under which the control hybrid protein is expressed in sufficient quantity for the second detectable signal to be produced;
g) determining whether either or both of the detectable signals are produced.

The method thus provides a rapid and straightforward way of removing false positives arising from interactions between test proteins and detection domains.

Usually, step f) is performed once a positive signal has been detected following step e), in order to confirm whether or not the signal indicates a true positive interaction between the first and second test proteins. The detection of the signals in step g) may thus be carried out as an integral part of steps e) and f.

The detectable signal may be generated in a variety of different ways. Preferably, the first and second detectable signals are produced by means of activation of first and second reporter genes. A reporter gene can be any gene encoding a detectable polypeptide product, whether it be detectable by means of a positive indicator eg. a colour change, or by selection for growth.

It is envisaged that the invention may be performed in a variety of different systems. Preferably, the invention is performed as a modified two-hybrid assay in which:
  b) (ii) the first detection domain comprises a first DNA-binding domain which recognises a DNA binding site on the first reporter gene;
  c) (ii) the second detection domain comprises a transcriptional activation domain; and
  d) (ii) the control detection domain comprises a second DNA-binding domain which recognises a DNA binding site on the second reporter gene;
wherein the reporter genes are activated by the transcriptional activation domain when this is in sufficient proximity to the reporter genes, and the DNA binding sites on the reporter genes are different.

False positives of type 1 above are thus also eliminated. The use of two different reporters acted on by two different DNA-binding domains gives a rapid and easy to use assay.

The DNA binding site is the site generally referred to as the operator in prokaryotic systems, and the upstream activating sequence (UAS) in eukaryotic systems.

The use of the term "control" herein in relation to the control chimeric gene, control hybrid protein and control detection domain does not exclude there being other, standard controls employed in the method according to the invention. Indeed, in any assay of this nature a number of controls will be needed in order that meaningful results are obtained.

It may be preferable in the modified two-hybrid assay according to the invention, to use first and second reporter genes which have different promoters as well as different binding sites for the DNA-binding domains. In that case, the different promoters have as far as possible no DNA binding motifs in common (all promoters contain a TATA box which binds the TATA factor prior to initiation of transcription by RNA Polymerase II). This will ensure that all false positives of type 1 are eliminated. However, the invention can also be performed using two promoters which are the same or similar, provided that the DNA binding motifs are different. A promoter minus the DNA binding motif may be referred to as a basal promoter.

Preferably, the first hybrid protein and the control hybrid protein lack any protein binding sites in common other than protein binding sites specific to the first test protein. Protein binding sites are sequences which are capable of taking part in protein-protein interactions. This lack of sequence similarities ensures that false positives falling into classes 2 and 3 above are eliminated.

Preferably, the modified two-hybrid assay according to the invention is performed in yeast, such as Saccharomyces cerevisiae or Schizosaccharomyces pombe. It is a further preferred feature of the assay that step f), which is the step of introducing the control chimeric gene into the host cell, is performed by mating haploid yeast cells of opposite mating type, one yeast cell mating type containing the first reporter gene and chimeric genes which encode the first and second hybrid proteins, and an opposite yeast cell mating type containing the second reporter gene and a chimeric gene which encodes the control hybrid protein.

In a second aspect, the invention provides a method as herein described for a modified two-hybrid assay, wherein the first hybrid protein and the control hybrid protein are in the form of a single dual hybrid protein, comprising the first test protein and the two different DNA-binding domains. In such a method, the first and second test proteins may both be derived from cDNA libraries. The method may thus be particularly useful for screening two cDNA libraries against each other to identify genes coding for proteins that interact with one another, while avoiding false positives of type 1 a described above.

In a preferred embodiment according to this second aspect of the invention, and in particular for a library versus library screen, step f), that is the contacting of the dual hybrid protein (first test protein plus two DNA-binding domains) with the second hybrid protein (second test protein plus transcriptional activation domain), is performed by mating haploid yeast cells of opposite mating type, one containing a chimeric gene encoding the dual hybrid protein and at least one of the reporter genes and another containing a chimeric gene encoding the second hybrid protein and at least the other reporter gene. In a particularly preferred embodiment, each of the opposite mating type yeast cells contains both the first and second reporter genes.

The term "two-hybrid assay" as used in connection with the present invention is not intended to be limited to any specific two-hybrid system according to Fields and Song(1). The-modified two-hybrid assay according to the invention preferably includes the following general steps:

a) providing a host cell containing a first reporter gene under the control of a first promoter which is activated by a transcriptional activation domain;
  b) providing a first chimeric gene that is capable of being expressed in the host cell, the first chimeric gene comprising a DNA sequence that encodes a first hybrid protein, the first hybrid protein comprising:
     (i) a first test protein that is to be tested for interaction with a second test protein;
     (ii) a DNA-binding domain that recognises a binding site on the first promoter;
  c) providing a second chimeric gene capable of being expressed in the host cell, the second chimeric gene comprising a DNA sequence that encodes a second hybrid protein, the second hybrid protein comprising:
     (i) a second test protein that is to be tested for interaction with the first test protein; and
     (ii) the transcriptional activation domain;
wherein an interaction between the first test protein and the second test protein in the host cell causes the transcriptional activation domain to activate transcription of the reporter gene;
  d) introducing the first chimeric gene and the second chimeric gene into the host cell;
  e) subjecting the host cell to conditions under which the first hybrid protein and the second hybrid protein are expressed in sufficient quantity for the detectable gene to be activated;
  f) determining whether the detectable gene has been expressed;
  g) further providing a second reporter gene under the control of a second promoter which is activated by a transcriptional activation domain, said second promoter having a different DNA binding site to the first promoter and preferably also lacking as far as possible any DNA binding motif in common with the first promoter in the basal portion of the promoter;
  h) further providing a control chimeric gene that is capable of being expressed in the host cell, the control chimeric gene comprising a DNA sequence that encodes a control hybrid protein, the control hybrid protein comprising:
     (i) the first test protein;
     (ii) a DNA-binding domain that recognises a binding site on the second reporter gene:
  (i) introducing the control chimeric gene and the second reporter gene into the host cell;
  (i) subjecting the host cell to conditions under which the control hybrid protein and the second hybrid protein are expressed in sufficient quantity for the second reporter gene to be activated; and
  (k) determining whether the second reporter gene has been expressed to confirm whether the first and second test proteins interact.

The first and second test proteins as referred to herein, when in the context of the two-hybrid system, may be understood to correspond to the bait protein and the protein of interest respectively. In a library versus library screen, the first test protein is the unknown protein in a hybrid with the DNA-binding domain(s) and the second test protein is the unknown protein in a hybrid with the activation domain.

The chimeric genes encoding the first, second and control hybrid proteins will usually be present in expression vectors such as plasmids. Expression vectors which can easily be transferred between systems are preferred. The expression vectors will require markers to indicate their presence in a host cell. Preferred markers are markers which can be selected for such as auxotrophic markers or markers which confer antibiotic resistance. It will be evident that a different marker will be needed for each of the chimeric genes as these are all present in the host cell at one time.

In another aspect the invention provides a method of performing a two-hybrid assay in yeast, which method comprises mating two yeast cells of opposite mating type, the yeast cells respectively comprising (i) a first chimeric gene encoding a hybrid protein comprising a first DNA-binding domain and a first test protein, a second chimeric gene encoding a hybrid protein comprising a transcriptional activation domain and a second test protein, and a first reporter gene having a DNA binding site recognised by the first DNA-binding domain; and (ii) a third chimeric gene encoding a hybrid protein comprising a second DNA-binding domain and a third test protein, and a second reporter gene having a DNA binding site recognised by the second DNA-binding domain, the first and second DNA-binding domains and DNA binding sites being different; and determining whether the reporter genes are expressed.

Another possible use of this method in addition to screening for false positives is to enable two linked protein protein interactions occurring simultaneously in a single cell to be detected. This could be useful in the study of signal transduction pathways. For example if protein A interacts with protein B which in turn interacts with protein C, it would be possible to construct a first chimeric protein containing gene B. The second and control or third chimeric genes could contain gene A and gene C respectively. Transformation of the first and second chimeric genes into a yeast cell containing the first reporter allows the interaction between protein A and B to be studied. The control or third chimeric gene and the second reporter could then be introduced and the interactions between protein A, protein B and protein C examined.

Further aspects of the invention include kits containing some or all of the reagents required for performing an assay according to the invention.

A suitable kit according to the invention may comprise:
  (a) two different bait vectors capable of expressing two different hybrid proteins comprising different DNA-binding domains and a first test protein, each vector comprising a nucleic acid sequence which encodes one of the DNA-binding domains and an insertion site for a nucleic acid sequence encoding the first test protein; or
  (b) a single bait vector capable of expressing a dual bait hybrid protein comprising two different DNA-binding domains and a first test protein the vector comprising nucleic acid sequences which encode the DNA-binding domains and an insertion site for a nucleic acid sequence encoding the first test protein; and
  (c) an activator vector capable of expressing an activator hybrid protein comprising a transcriptional activation domain and a second test protein, the vector comprising a nucleic acid sequence which encodes the activation domain and an insertion site for a nucleic acid sequence encoding the second test proteins; and
  (d) two reporter genes capable of producing different detectable signals, each reporter gene having a DNA binding site for one of the DNA-binding domains encoded by the bait vector or vectors.

Alternatively, the activator or bait vectors, or both, may already contain sequences encoding the test proteins, eg. from a cDNA library.

The reporter genes in the kit according to the invention may be contained in plasmids. Preferably however they are integrated into yeast cells of opposite mating type.

The term "test protein" as used herein is considered to include peptides, polypeptides and related molecules including for example antibody binding fragments. One or both of the test proteins may consist of a fragment of a particular protein of interest.

Although the preferred host cells for use in the assay according to the invention are yeast cells, the invention may also be applied to two-hybrid screens in mammalian cells, insect cells, plant cells or any intact eukaryotic or prokaryotic organism. In particular with use of yeast cells, the assay method will be capable of automation. It is envisaged that the removal of false positive interactions and the speed and ease of mating between two haploid yeast cells will make it feasible to perform analysis of protein-protein interactions with higher throughput. This makes automation an attractive facility.

The use of two haploid yeast strains is a preferred but not essential part of the invention. In an alternative embodiment, a whole screening system may be set up in a single haploid or diploid strain which contains at least two reporter genes and has been transformed with the appropriate chimeric genes.

Other types of two-hybrid system can be envisaged which do not depend for their end point on transcriptional activation. The principle of the present invention as applied to two-hybrid systems, that different hybrid proteins comprising the same bait protein are screened so that activation of two measurable end points results, is also applicable to these types of two-hybrid assays.

When transcriptional activation of reporter genes is employed in the method according to the invention to provide the necessary detectable signals, at least two reporter genes with different DNA binding sites are required. Further reporters may also be used, which can be of any suitable type (measurable or selectable). Overall, the reporter gene promoters may share sequences in common, provided of course that no single DNA binding site is present in all of the reporter gene promoters which are employed. Preferably, the reporter gene promoters are different.

Reporter genes whose expression can be detected by simple means such as inclusion or exclusion of certain reagents in the growth medium of the host cell or observation of a colour change, are preferred. Suitable reporter genes will be known to those skilled in the art. Reporter systems which may be used for the first and second reporter genes in the method according to the invention include but are not limited to auxotropic markers such as Histidine, β-galactosidase (lacZ), luciferase, green fluorescent protein (GFP) and Ubiquitin (8). The reporter may be any gene which encodes a fluorescent protein, bioluminescent protein, an enzyme which catalyses the formation, modulation or destruction of a fluorescent or bioluminescent molecule. Alternatively a protein (such as an apoprotein) that binds to a bioluminescent or fluorescent molecule (such as a prosthetic group). A gene that encodes a protein that modifies another molecule (such as another protein) which ultimately results in a chromogenic, fluorescent or bioluminescent change. An advantage of the ubiquitin system is that it allows monitoring of protein-protein interactions as a function of time. Also, the interactions can occur in the cytoplasm as opposed to the nucleus (in the conventional two-hybrid approach, the interaction must occur in the nucleus).

Suitable detection domains for the hybrid proteins in the method according to the invention have been described so far only with reference to two-hybrid assays. Other suitable detection domains envisaged include fluorescent moieties or moieties capable of becoming fluorescent. Such detection domains may work in the invention in the following way. The first and second detection domains, when in sufficiently close proximity, cause the emission of light at a particular wavelength. The second detection domain and the control detection domain, when in sufficiently close proximity to one another, cause light of a different wavelength to be emitted. The first and control detection domains may thus each be a different fluorescent moiety for which the wavelength is altered when the moiety is in close proximity with the second detection domain. Alternatively, the second detection domain is a fluorescent moiety for which the wavelength of the light emitted is altered to a different extent by proximity to the first and second detection domains respectively. In this type of system the first and second detectable signals are light emitted at different wavelengths.

The term DNA binding motif is used herein to describe a DNA binding site to which a protein, such as a DNA-binding domain in the method according to the invention, is capable of binding. Suitable reporter genes, promoters, DNA-binding and activation domains etc. for use in the invention will be known to those skilled in the art.

Previously, three DNA-binding domains have been commonly used in variants of the two-hybrid or interaction trap system. These include the Gal4p DNA-binding domain (1), the LexA DNA-binding domain (9), and the serum response factor DNA-binding domain of SRF (10). These DNA-binding domains have never previously been used together in a dual bait two-hybrid system nor are there any examples of two DNA-binding domains being used together in a single cell in a two-hybrid system for removal of false positives.

DETAILED DESCRIPTION OF THE INVENTION

In detail the invention may be used practically in the following way, which exemplifies the principles of the invention described above:

In the first part of the false positive elimination system, the principles of present state of the art two-hybrid systems are applied. This consists of the use of two reporter genes, a selectable reporter (eg.HiS3) and a measurable reporter (eg. lacZ). These reporter genes are placed in a haploid yeast strain under the control of promoters containing a specific upstream activating sequence (UAS) or DNA binding site (eg. the lexAo DNA binding sequence (9). This sequence is placed adjacent to a basal promoter sequence which lacks a UAS (eg. basal sequences from the CYC1, GAL1 or HIS3 promoters). These reporter constructs will preferably be integrated into the yeast genome, but this is not a necessary part of the invention. The strain is transformed with a chimeric bait construct so that it expresses a bait hybrid protein comprising the bait protein domain fused to a DNA-binding domain (eg. the lexA DNA-binding domain). The strain is also transformed with a further library of constructs which contain a set of chimeric activator genes, expressing a cDNA library fused to a DNA sequence encoding a transcriptional activation domain (eg. the GAL4 activator sequence). In this strain those colonies which express both the measurable and selectable reporter genes will be expressed. The use of a single strain with two reporter genes for identification of two-hybrid interaction proteins expressed from single activator and bait constructs is representative of the state of the art prior to the present invention.

For the present invention a second haploid yeast strain of opposite mating type is a preferred component. This strain contains a reporter gene which is preferably integrated into its genome. This reporter gene could be either a selectable or measurable reporter gene (or two reporter genes representing one of each type could also be used). In the preferred example a measurable reporter gene is used, such as the GFP gene or a luciferase-encoding gene. The reporter gene in the second strain is under the control of a different basal promoter sequence to the reporter genes in the first strain (eg. GAL1 instead of CYC1). This promoter also contains a different UAS which is a specific DNA binding site (such as SRE instead of lexAo). This means that there is as far as possible no similarity in sequence between the promoters in the first and second strains. It is a preferred feature of this invention that while any two promoters may share sequence sirmilarity, no single sequence element is present in each of the promoters in front of the reporter genes. A second bait hybrid protein will be expressed in the second strain which contains a different DNA-binding domain to that in the first strain and which is specifically able to bind to the DNA binding site in front of the reporter gene in the second strain (i.e. SRF which binds to SRE). Any epitope tags or intervening coding sequences between the DNA-binding domain and the bait protein will preferably be different to the first bait hybrid protein so that apart from the bait protein there are as far as possible no other sequence similarities between the two bait proteins. The second yeast strain may be mated to the first strain to produce a diploid strain. If the protein of interest participates in a specific interaction with the bait protein, then the diploid strain will express all three reporter genes. Only a true positive can give rise to expression of all three reporter genes. This strategy removes each of the classes of false positives that arise from interactions between molecules other than the protein of interest and the bait protein.

As well as screening for false positives in cDNA library screens in the two-hybrid system this approach will have particular utility when screening random peptide libraries (11) and antibody binding site libraries. Such libraries contain peptides of random sequence composition which may be screened in the two-hybrid system in order to identify those which bind specifically to the bait protein of interest. Since they are random, there is an equal chance of a peptide occurring which binds to the bait protein domain of interest as there is of a peptide occurring which binds to the DNA-binding domain. The present invention will remove such false positives efficiently.

A further application of the invention to the two-hybrid system is for screening two libraries against each other in order to identify pairs of unknown interacting proteins. This approach may have a major application for identification of unknown gene function resulting from the human genome sequencing and mapping projects. Here, the removal of false positives is critical due to the large number of anticipated protein interactions which will be identified. Since in this approach the bait protein is unknown and is replaced by a second cDNA library, it is not possible to prepare matching strains transformed with bait chimeric constructs encoding pairs of bait hybrid proteins. Therefore, a modification to the above invention is described below which is based on the same novel principle described above.

For screening two libraries, the following method may be used. Two yeast strains are required which are similar to those described above. They contain a total of at least three reporter genes, at least two of which have promoters with entirely different sequences placed in front of the reporter genes. A first cDNA library is fused to the activator domain and the resulting set of chimeric genes are transformed into the first haploid strain. No activation of any reporter gene should occur in this strain at this stage since no bait is present, but if a DNA-binding domain has been fused to the activator domain, there may be activation of a reporter gene. A second cDNA library is then fused to two DNA-binding domains joined together in the same protein to prepare a dual hybrid bait protein. This library is transformed into the second bait strain. At this stage a number of clones in the library may contain gene sequences encoding proteins which have transcriptional activation domains of their own. These will give rise to reporter activation in the haploid strain. Colonies encoding clones of the activator library which show activation of the reporter in the first yeast strain and clones of the bait chimeric library which show activation of the reporter in the second yeast strain should then be selected out from the library eg. by the use of a reporter gene in each strain whose expression can be selected against (such as Ura3p which can be selected against using 5-Fluoro-orotic acid (5-FOA)). The two haploid yeast strains can then be mated and resulting diploid strains which express each of the reporter proteins selected for and analysed. This will give rise to a bank of yeast colonies expressing interacting pairs of proteins which are substantially free from false positives. False positives which may occur in the library vs library screening strategy are those activator library proteins that bind to the DNA-binding portion of the chimeric bait protein, or possibly bait proteins that bind to the activator domain of the chimeric activator protein. Further analysis using the preparation of single bait hybrid proteins from the known proteins as described above, will largely exclude this class of false positives.

The elimination of false positives is essential for the analysis of interacting proteins by library versus library screening in the two-hybrid system. Efficient removal of false positives will permit high throughput automation of the screening process.

The present invention is directed in particular to the screening of DNA libraries against known proteins, or against DNA libraries, to detect interacting proteins. The false positives which may arise when using a known bait protein to screen a library have been discussed above, numbered 1 to 4. The additional false positives which may be encountered when one library is screened against another are:

5. A transcriptional activator might be cloned into the DNA-binding hybrid which would activate transcription independently of the activator hybrid;

6. Protein encoded by the bait hybrid might bind to the activation domain of the activator hybrid.

Schemes for reducing or eliminating false positives in these classes, will be described below. These may apply to library versus library screening only, or single library screening also. All of these schemes are based on the two-hybrid system.

I. Removal of False Positives from Libraries Prior to Mating (i) Removal of DNA-binding domains and transcriptional activation domains from library clones.

This scheme removes false positives from groups 1(a), 1(b) and 5 in the list above. Yeast strains of opposite mating type are provided which contain a reporter such as Ura3p that can be selected against, under the control of a promoter to which the DNA-binding domain of the bait construct binds. The library hybrids (bait/library and act/library) can be introduced into the strains and any clones which activate the Ura3p reporter can be selected against using 5-FOA. The remaining viable yeast clones can be mated to identify true positives.

(ii) Removal of DNA-binding domains and transcriptional activation domains from library clones together with any clones which bind to the DNA-binding domain of the bait hybrid vector and any clones which bind to the activation domain of the activator vector.

This scheme involves an empty bait (i.e. DNA-binding hybrid minus the library protein) and an empty activator (i.e. activation hybrid minus the library protein). This is a further development of (i) above which removes false positives in classes 1(a), 1(b), 2, 5 and 6. Preferably it is performed following (i) above for comprehensive removal of false positives. It could be used in both a single library screen and a library versus library screen. The strains of opposite mating type for this scheme applied to library versus library screening contain act/library, empty bait and reporter; and bait/library, empty activator and reporter, respectively.

II. An Alternative Scheme for Removing DNA-binding Domains and Transcriptional Activation Domains from Library Clones Post Mating This scheme involves the use of an inducible yeast promoter driving the activator hybrid. A key point is that the two reporters have the same basal promoter such as GAL1 but different specific DNA binding sites. Note that the bait has to contain a single DNA-binding domain for this scheme because it relies on a second reporter to remove false positives as described below.

To illustrate, a suitable set of components for performing this assay could comprise inducible promoter/activator hybrid, lexA/bait hybrid, lexA/GAL basal p/reporter 1, and SREIGAL basal p/reporter 2, all present in a host cell.

A true interaction will result in expression of reporter 1 but not reporter 2 under inducing conditions. In non inducing conditions, both reporters would be switched off.

A false positive is present if the first reporter is expressed when cells are grown under non inducing conditions. In this situation, the activator hybrid is "off" or expressed at very low levels. It is possible to screen out activation domains inadvertently cloned as part of a library into the bait hybrid vector by plating the cells with negative selection under non inducing conditions.

In the alternate case there may be general DNA-binding clones in the activator hybrid library which bind to the basal region of the promoter e.g. TATA binding proteins. A false positive would result in expression of reporter 2, under inducing conditions.

It is possible to select against expression of reporter genes such as URA3; in this way both sets of false positives described above could be removed from the libraries. False positives in classes 1(a), 1(b) and 5 are removed.

EXAMPLES

Application of this Invention

The invention will allow the removal of two principle classes of false positives which are not fully removed by current two-hybrid systems without time-consuming methods which involve plasmid curing and plasmid rescue.
1. Those proteins which bind to a specific element in the promoter. In particular, those proteins which interact with the UAS sequence (eg. LexAo or SRE).
2. Those proteins which interact with the DNA-binding domain of the bait protein or other sequences present in the bait protein which are not specifically present in the bait protein domain of interest.

The use of two DNA-binding domains in dual bait proteins allows the use of two or more independent reporter genes which do not have promoter sequences in common. The Examples which follow show that this principle can be applied to removing both classes of false positive.

Example 1

Identification of a False Positive Arising from a Protein that which Interacts with the Reporter Gene Promoter Sequence The following example illustrates the identification of a false positive in a yeast 2-hybrid assay without the need to cure plasmids from yeast. This false positive arises due to direct interaction with the reporter gene promoter.

SRE is a mammalian growth factor responsive element which binds a ubiquitous serum response factor SRF (23). SRF would be encountered as a false positive in the 2-hybrid assay when screening a mammalian library cloned into the activator plasmid if the enhancer element SRE forms part of the reporter gene promoter. In this situation, SRF would be fused to a transcription factor activation domain such as Gal4p. This second hybrid protein can induce expression of the reporter gene in the absence of a first hybrid protein or bait protein.

To illustrate the occurrence of SRF as a false positive in a 2-hybrid assay, two chimeric yeast plasmids are produced. The plasmid expresses a bait protein of interest such as ATF2 (24) fused to the DNA binding domain SRF. The second chimeric plasmid expresses the SRF is binding domain (which mimics a human library clone) fused to a transcription factor activation domain such as VP16 or Gal4. The first reporter gene construct contains SRE, a basal promoter such as CYC1 and a reporter gene such as firefly luciferase. These three constructs are introduced into a suitable yeast strain such as YM4136 (MATα ura3-52 his3-200 ade2-101 lys2-801 trp1-901 leu2-3, 112 gal80-538—a gift from M. Johnston). The first hybrid protein alone cannot activate expression of the first reporter gene construct. However, when the first and second hybrid proteins are co-expressed, increased expression of the first reporter gene is observed.

In order to ascertain whether the expression of the first reporter gene is due to an interaction between ATF2 and SRF or to direct activation via the second hybrid protein, two further plasmids are produced. A control plasmid is constructed containing an alternate DNA binding domain such as the bacterial repressor lexA fused to ATF2 together with a second reporter construct containing lexAo-GAL1-HIS3. The control chimeric construct and the second reporter construct are introduced into a suitable yeast strain of opposite mating type such as YM4133 (MATa ura3-52 his3-200 ade2-101 lys2-801 trp1-901 leu2-3, 112 gal80-538—a gift from M. Johnston) The two strains are mated and diploid cells are selected. The diploid yeast are unable to grow on histidine deficient media and therefore have a His-phenotype, indicating that SRF is a false positive, without having to remove the first chimeric gene.

Example 2

Identification of False Positives Arising from Interactions between the Protein of Interest and the DNA Binding Domain of the Bait Plasmid The table below shows the chimeric genes and reporters used in this example.

| | |
|---|---|
| First chimeric gene | SRF-ATF2 |
| Second chimeric gene | VP16-SAP1 |
| Control chimeric gene | LexA-ATF2 |
| Reporter gene 1 | SRE-GAL1-luciferase |
| Reporter gene 2 | lexop-GAL1-HIS3 |

The following example illustrates the identification of a false positive which binds to the detection domain of the first hybrid protein without the need to cure plasmids from yeast. In this case, the gene of interest is ATF2 (24) which is cloned into a "bait" plasmid containing the SRF DNA binding domain. The plasmid is introduced into a suitable yeast strain such as YM3146 (YM4136 genotype MATα ura3-52 his3-200 ade2-101 lys2-801 trp1-901 leu2-3, 112 gal80-538

-gift from M. Johnston), resulting in the expression of a hybrid protein: SRF DNA binding domain-ATF2. A plasmid encoding the reporter gene SRE-GAL1-luciferase and a plasmid which expresses the hybrid protein VP16-SAP1 are also transformed into the same yeast strain. This results in an increase in the expression of luciferase, due to the binding of SAP1 to SRF (23). ATF2 is not known to interact with SAP1; therefore SAP1 is a false positive.

A plasmid, which expresses the control hybrid protein (LexA DNA binding domain-ATF2) and a second reporter gene (lexAo-GAL1-HIS3 are introduced into a suitable yeast strain of opposite mating type such as YM4133 (genotype MATa ura3-52 his3-200 ade2-101 lys2-801 trp1-901 leu2-3, 112 gal80-538—gift from M. Johnston).

The YM4133 transformant is mated with the YM4136 transformant and diploid yeast are selected. The diploids are plated on media in the absence of histidine. The diploid yeast are unable to grow on histidine deficient media and therefore have a His⁻ phenotype, indicating that SAP1 is indeed a false positive. Note that there is no need to remove the first chimeric gene in order to ascertain that SAP1 is a false positive.

Example 3

Introduction

Example 3 illustrates the use of the invention to discriminate between true positives and false positives which have arisen from the library screen. A control chimeric gene, which in this example expresses a Gal4p DNA-binding domain-ATF2 hybrid protein, and a second reporter is introduced into a cell containing the first and second chimeric genes as well as the first reporter. Analysis of the expression of the second reporter enables the true positives to be distinguished from the false positives.

Methods

Construction of Plasmids

The construction of the plasmids was by standard procedures (12). Purification of DNA was carried out using Qiagen columns. Enzymes were obtained from Amersham International unless otherwise stated. Oligonucleotides were synthesised by Genosys (Cambridge, UK). Bacterial host used was E.coli strain pMosBlue (Amersham) (endA 1 hsdR17($r_{k12}m_{k12}^+$)supE44thi-1 recA1 gyrA96 relA1 lac(F' proA⁺B⁺lacI $^q$ZΔM15::Tn10(TC$^R$) or NM554 (F⁻araD139 Δ(ara-leu)7696 galE15 galK16 Δ(lac)X74 rpsL (Str$^r$)hsdR2 ($r^-_k m_k^+$) mcrA mcrB1 recA13.

Growth of Yeast

Standard methods for the growth of *Saccharomyces cerevisiae* was used (13). Yeast was transformed by the lithium acetate method (14). FOA plates included 1 g/l of 5-FOA (Sigma) (15).

Assembly and Functional Testing of Yeast Reporters 1 and 2

The construction of the first and second reporters is described. Also described are the construction of the two yeast strains used in the invention. These yeast strains are of opposite mating type. One strain ySD2 is a strain derived from YM4136 (M. Johnston). The GAL4 has been knocked out in this strain. The second strain yDM2 is based on YM4136 (M. Johnston) and contains the second reporter integrated into the GAL4 thereby inactivating the GAL4. The construction of reporters 1 and 2 and the two yeast strains are described below. The functional testing of the GAL1-luciferase is described.

The reporters are under the control of two different upstream activation sequences (UAS), either a lexAo or a GAL4 DNA binding sequence. The reporters produce signals which are distinguishable from each other. The first reporter is a HIS3 gene which on expression in a his3 yeast cell produces a yeast cell which is His+. The second reporter used is the firefly luciferase which produces light in the presence of ATP, oxygen and luciferin. The integration of the GAL1-luciferase into the yeast genome is described, as well as the construction of a gal4 yeast strain.

Constructions

Construction of the First Reporter

The first reporter was constructed as follows. The GAL1 basal promoter was amplified by a polymerase chain reaction (PCR) using the plasmid pWitch (WO 96/30507) as the template and the primers 5'-GCGCGCGAGCTCGAGC MTAAAGATTCTACMTACTAGC-3' (SEQ ID NO: 1) and 5'-GGCCCGGAATTCGTCGACAGTCMGATCTTA TAGIITTTICTCCTTGA CGTT-3' (SEQ ID NO: 2). The PCR fragment was cut with XbaI, treated with T4 DNA polymerase and then digested with SacI. The plasmid pV44ER-Lex (16) was cut with EcoRI, treated with T4 DNA polymerase digested with SacI, resulting in the excision of the GAL UASICYC1 promoter-LexA DNA binding domain. The fragment produced by the PCR was ligated to the remaining pV44ER-Lex fragment, to create the plasmid pSD1. PSD1 contains the GAL1 basal promoter, a unique EcoRI site followed by the CYC1 transcriptional terminator. The HIS3 gene was amplified by PCR using the primers 5'-GCGCGCGGATCCAAAATGACAGAGCAGAAAG CCC-3' (SEQ ID NO: 3), 5'-GGCCGCGMTTCCGGTG TCACTACATMGMC-3' (SEQ ID NO: 4) (EcoRI and BamHI sites underlined) from pRS413 (17). The PCR product was cut with EcoRI and BamHI, then treated with T4 DNA polymerase, and inserted into pSD1 pre-treated with EcoRI and T4 DNA polymerase. This construct was called pSD2. Oligonucleotides containing the lexA operator were synthesised (5'-TCGACTGCTGTATATAAAACCA GTGGTTATATGTACAGTACG-3' (SEQ ID NO: 5) and 5'-TCGACGTACTGTACATATMCCACTGGTTTTATAT ACAGCAG-3' (SEQ ID NO: 6))(18). The oligonucleotides were annealed and cloned into the XhoI site of pSD2. A clone was selected containing 3 copies of the lexA operator. This clone was called pSD6. The lexAo-HIS3 fragment of pSD6 was swapped to a plasmid backbone containing an ADE2 selectable marker. PSD6 was cut with PvuII to release the lexAo-HIS3 containing fragment. This fragment was cloned between the PvuII and SmaI sites of pASZ11 (19) to create pDM68. The plasmid pDM68 therefore contains the first reporter, in this case lexo-GAL1-HIS3.

Construction of the Second Reporter

The firefly luciferase gene was excised from the TNT control vector (Promega) with the enzymes HindIII and SacI, blunted and cloned into a blunted EcoRI site in pSD1 to create pMW60. The fragment of the GAL1-10 upstream activating sequence (UAS) which contains the Gal4p DNA binding sequence was then subcloned into pMW60 as follows. The GAL1-10 UAS fragment was amplified by a PCR using as pWitch (WO 96/30507) a template and the primers: 5'-GGCTCGAGGTCGACGMGTACGGATTAGAAG CC-3' (SEQ ID NO: 7) and 5'-GGCTCGAGTTCGGAG CAGTGCGGCG-3' (SEQ ID NO: 8). (The two XhoI sites are underlined in the primer sequences). These primers bind to basepairs 362–380 and 471–487 of the GAL1-10 promoter (Genbank accession number k022115). The amplified fragment was cut with XhoI and inserted into the XhoI site of pMW60 to create the plasmid pDM57. The GAL1- luciferase was then subcloned into a plasmid containing a LYS2 selectable marker by excising the reporter using the restriction enzyme BglI and cloning it between the two BglI sites of pRS317 (obtained from the ATCC) to produce pDM58.

Testing the GAL1-HIS3

In order to ensure that the GAL1-HIS3 reporter was functional, the reporter was tested in a 1-hybrid assay. The plasmid pSD2 or pSD6 were transformed into YM4136 genotype MATα ura3-52 his3-200 ade2-101 lys2-801 trp1-901 leu2-3, 112 gal80-538 (gift from M. Johnston) along with the 1-hybrid activator V152 (gift from Nic Jones). The plasmid V152 expresses an E1A transcriptional activation domain-LexA DNA binding domain hybrid protein. Yeast co-transformed with pSD2 and V152 grew poorly on His⁻ media, whilst yeast containing pSD6 and V152 grew well on histidine deficient media. This demonstrated that the GAL1-HIS3 was functional in a 1-hybrid assay.

Testing the GAL1-luciferase

In order to show that the second reporter was expressed in yeast a one hybrid assay was carried out. The one hybrid plasmid pCL1 was obtained from Clontech and it express the full length Gal4p in yeast. As a control the plasmid pMW64 was used. This plasmid is identical to pDM57 except it contains a single lexA operator inserted into the XhoI site instead of the Gal4p DNA binding sites. The yeast strain Hf7c genotype MATa ura3-52 his3-200 lys2-801 ade2-101 trp1-901 leu2-3, 112 gal4-542 gal80-538 LYS2::GAL1-HIS3 URA3::(GAL4 17mers)$_3$-CYC1-lacZ (20) was transformed with pCL1 and pDM57 or pMW63. Co-transformants were grown up and the luciferase activity assayed as follows: 1.5 ml of culture was spun in a microfuge for 2 minutes, the supernatant removed and the pellet resuspended in 200 µl of citrate buffer pH 4.0. The relative light units were recorded using a Berthold Lumat luminometer. 100 µl of 0.56 mg/ml luciferin (USB, Cleveland, Ohio) solution in 25 mM Tris-phosphate pH 7.75 was injected and the highest number of relative light units (RLU) reached over 2 minutes was recorded. The results are shown in Table 1 below.

TABLE 1

| Plasmids transformed | optical density (OD) of culture at 600 nm | RLU | RLU/OD |
|---|---|---|---|
| pCL1 + pDM57 | 0.34 | 37,855 | 111,338 |
| pDM57 | 0.32 | 63 | 197 |
| pCL1 + pMW64 | 0.28 | 15 | 54 |
| pCL1 | 0.504 | 16 | 32 |
| No yeast | — | 12 | — |

The results of this experiment indicate that the GAL1-luciferase is functional and expression of the luciferase can be detected in yeast.

The Construction of the Yeast Strains

The two strains are based on YM4136 and YM4133 genotype (MATa ura3-52 his3-200 ade2-101 lys2-801 trp1-901 leu2-3, 112 gal80-538) (gift from M. Johnston).

In order for the Gal4 two hybrid system to function correctly it was first necessary to remove the endogenous Gal4p present in the yeast cell. This was carried out by deleting part of the chromosomal GAL4. The GAL4 gene (Genbank accession number k01486) was amplified by PCR using yeast genomic DNA as a template and the primers 5'-CGTCCTTTGAGACAGCATTC-3' (SEQ ID NO: 9) and 5'-GTTACATGGCCAAGATTGAAAC-3' (SEQ ID NO: 10). These primers bind to basepairs 165–184 and 3208–3229 of the GAL4 gene respectively. The fragment was cloned into the pMos Blue T vector (Amersham) to create pMos.GAL4. The *Kluyveromyces lactis* (*K.lactis*7) URA3 gene was then cloned between the BstX1 and SnaBI sites of the pMos.GAL4. The GAL4-URA3-GAL4 was excised from the pMos Blue backbone and transformed into the yeast strain YM4136. Yeast containing the *K.factis* URA3 integrated in the chromosomal GAL4 gene were selected. The yeast strain was then grown on media containing 5-FOA and a Ura⁻ mutant selected. This strain was gal4 and called ySD2.

The GAL1-luciferase was integrated into the GAL4 gene of the yeast strain YM4133 as follows: The GAL1-luciferase was excised from pDM57 using PvuII and cloned between the BsrBRI site (Promega) and the SnaBI site to create pDM64. The *K.lactis* URA3 was then cloned into the BclI site of the GAL4 to create a plasmid containing a GAL4-GAL 1-luciferase-GAL4-URA3-GAL4 cassette. This cassette was excised from the plasmid backbone using Sse8387I and BamHI (partial digest) and then transformed into the strain YM4133. A transformant which produced luciferase activity in the presence of pCL1, but no luciferase in the absence of pCL1 was selected. The yeast strain was then grown on media containing 5-FOA and a Ura– mutant selected. This strain was called yDM2.

Screening a Human Brain cDNA Library in a Yeast 2-Hybrid Assay Using ATF2 as a Bait.

Introduction

The chimeric gene 1 expresses the LexA DNA binding domain-ATF2 hybrid protein. This is used as a bait protein to screen a cDNA library which has been cloned into a 2-hybrid activator plasmid. Positives which arose in this screen (these could be true positives or false positives) were then analysed by using the invention.

The construction of the three chimeric genes are described. The first chimeric gene expresses a LexA DNA binding domain-ATF2 hybrid protein. This is used as a bait to screen a cDNA library. The screening of the cDNA library results in the isolation of several genes which may be true positives encoding proteins that interact with ATF2. Alternatively the genes isolated could be false positives. These are the second chimeric genes, expressing a hybrid protein consisting of the Gal4p activation domain fused to an unknown protein. The construction of the control chimeric gene is also described. In this example the control chimeric gene expresses a Gal4 DNA binding domain-ATF2 hybrid protein.

Construction of the First Chimeric Gene

The plasmid containing the first chimeric gene is based on the plasmid pDM26. This plasmid has been described previously (WO 96/30507) and expresses in yeast a LexA DNA binding domain. A kanamycin resistance gene was cloned into pDM26 by excising the kanamycin resistance gene from pUC4K (Pharmacia) with PstI. The fragment was cloned into the BglI and AatII sites of pDM26. The resulting plasmid was called pDM41. The ATF2 gene (a gift from Nic Jones) was then cloned into pDM41, at a position downstream of the LexA, in a two step process. Oligonucleotides (sequence AATTCCAGCTGG (SEQ ID NO: 11) and GATCCCAGCTGG (SEQ ID NO: 12), the PvuII site is underlined) were annealed and cloned between the EcoRI and BamHI sites of pDM41 to create pSD7. The ATF2 gene was excised using SalI and ClaI. The fragment was treated with T4 polymerase to create blunt ends and inserted into the PvuII site of pSD7, to produce the plasmid pSD12. The plasmid pSD12 therefore contained the first chimeric gene encoding, in this example, the LexA DNA binding domain fused to ATF2.

Construction of the Second Chimeric Gene

The activator plasmid is based on pDM22 (WO 96/30507). The plasmid pDM22 expresses the Gal4 transcriptional activation domain. This plasmid was modified by the addition of a F1 origin. The HindIII sites at the junction of the ADH1 promoter with the GAL4 activation domain and at the 5' end of the ADH1 terminator were removed by excising the HindIII fragment, treating the fragment with T4 DNA polymerase and reclining the blunted HindIII fragment back into the activator plasmid. This created a unique HindIII site in the polylinker. The cloning of a cDNA library into the activator plasmid is described below.

Construction of the Control Chimeric Gene

Two oligonucleotides were designed and synthesised with the sequence 5'-TATGMCCTGCAGGAAAGAATTCTG GATCCATGCGGCCGCGTGCA-3' (SEQ ID NO: 13) and 5'-CGCGGCCGCATGGATCCAGAATTCWTTCCTGCA GGTTCA-3' (SEQ ID NO: 14). The oligonucleotides were hybridised and cloned between the NdeI and PstI sites of the plasmid pAS2-1 (Clontech, Palo Alto). This plasmid was called pDM61. The ATF2 gene was excised from the plasmid pSD12 using the restriction enzymes Sse8387I and NotI and ligated to pDM61 cut with the same enzymes. This created the plasmid pDM62, which contains the control chimeric gene. In this case the control chimeric gene encodes the Gal4p DNA binding domain fused to the ATF2.

Isolation of Interacting Proteins and False Positives—Detection of the First Detectable Signal.

Proteins that interacted with ATF2 were isolated by carrying out a 2 hybrid screen of a human brain cDNA library. The two hybrid screen was carried out using a bait plasmid which expresses a LexA DNA binding domain-ATF2 hybrid fusion protein. The cDNA library was cloned into the EcoRI and HindIII sites of the activator plasmid. The reporter used was the lexAo-HIS3. 5 colonies that grew on media in the absence of histidine were isolated. This constitutes the detection of the first signal according to this invention. It was unknown at this stage whether these yeast contained activator plasmids encoding proteins that interacted with ATF2 or whether they were false positives. Two further experiments were carried out to judge if the yeast were true positives or false positives. The first experiment determined whether the yeast remained His+ after curing the bait plasmid from each strain. If the strains retained a His+ phenotype, the yeast were judged to be false positives. Second, the inserts in the activator plasmid were sequenced and checked for homology with public databases.

Confirmation of True Positives and Identification of False Positives Encountered in a Yeast 2-Hybrid Library Screen Without the Need to Cure Plasmids Introduction The second chimeric genes isolated as a consequence of the screening of the brain cDNA library could be true positives that encode proteins which interact with ATF2. Alternatively they could be false positives that encode proteins which do not interact with ATF2. The expression of the HIS3 obtained could be due to binding of the second hybrid protein directly to the lexAo or basal promoter of the first reporter. Alternatively the second hybrid protein could be binding to the LexA DNA binding domain of the first hybrid protein and not the ATF2 component. In this example the five chimeric genes isolated from the library have been mated to a strain containing the control chimeric gene and the second reporter, whilst still containing the first chimeric gene, to resolve whether they are true positives or false positives.

Mating

The yeast strain ySD2 which was transformed with the plasmid pDM68 (contains the first reporter), pSD12 (with the first chimeric gene) and one of the test activator plasmids (containing the second chimeric gene) was mated to the luciferase reporter strain yDM2 (containing the second reporter) previously transformed with pDM62 (with the third chimeric gene). Also mated to the ySD2 transformants were yDM2 transformed with either pDM61 or pLAM5'-1 (Clontech). The plasmid pLAM5'-1 contains the Lamin C gene cloned into pAS2-1. It therefore expresses a Gal4p activation domain-Lamin C hybrid protein. The Lamin C protein acted as an unrelated control. It is not expected that Lamin C protein would interact with proteins that bound to ATF2. These two matings per test acted as controls. Yeast strains were mated by innoculating 200 μl of YPD with the yeast of opposite mating types, incubating for 8 hours at 30° C. Diploids were selected on the adenine, trytophan, uracil and leucine depleted media. The plan for all yeast mating is shown in table 2 below.

TABLE 2

| Diploid strain | plasmids transformed in ySD2 | plasmid transformed in yDM2 |
|---|---|---|
| 1 | pDM68 and pDM22 | pDM62 |
| 2 | pDM68 and pDM22 | pLAM5'-1 |
| 3 | pDM68 and pDM22 | pDM61 |
| 4 | pDM68 and act#cJun | pDM62 |
| 5 | pDM68 and act#cJun | pLAM5'-1 |
| 6 | pDM68 and act#cJun | pDM61 |
| 7 | pDM68 and act#BS69 | pDM62 |
| 8 | pDM68 and act#BS69 | pLAM5'-1 |
| 9 | pDM68 and act#BS69 | PDM61 |
| 10 | pDM68 and act#polyA | pDM62 |
| 11 | pDM68 and act#polyA | pLAM5'-1 |
| 12 | pDM68 and act#polyA | PDM61 |
| 13 | pDM68 and act#FP2 | pDM62 |
| 14 | pDM68 and act#FP2 | pLAM5'-1 |
| 15 | pDM68 and act#FP2 | pDM61 |
| 16 | pDM68 and act#FP3 | pDM62 |
| 17 | pDM68 and act#FP3 | pLAM5'-1 |
| 18 | pDM68 and act#FP3 | pDM61 |

Detection of the Second Signal

Figure 1:
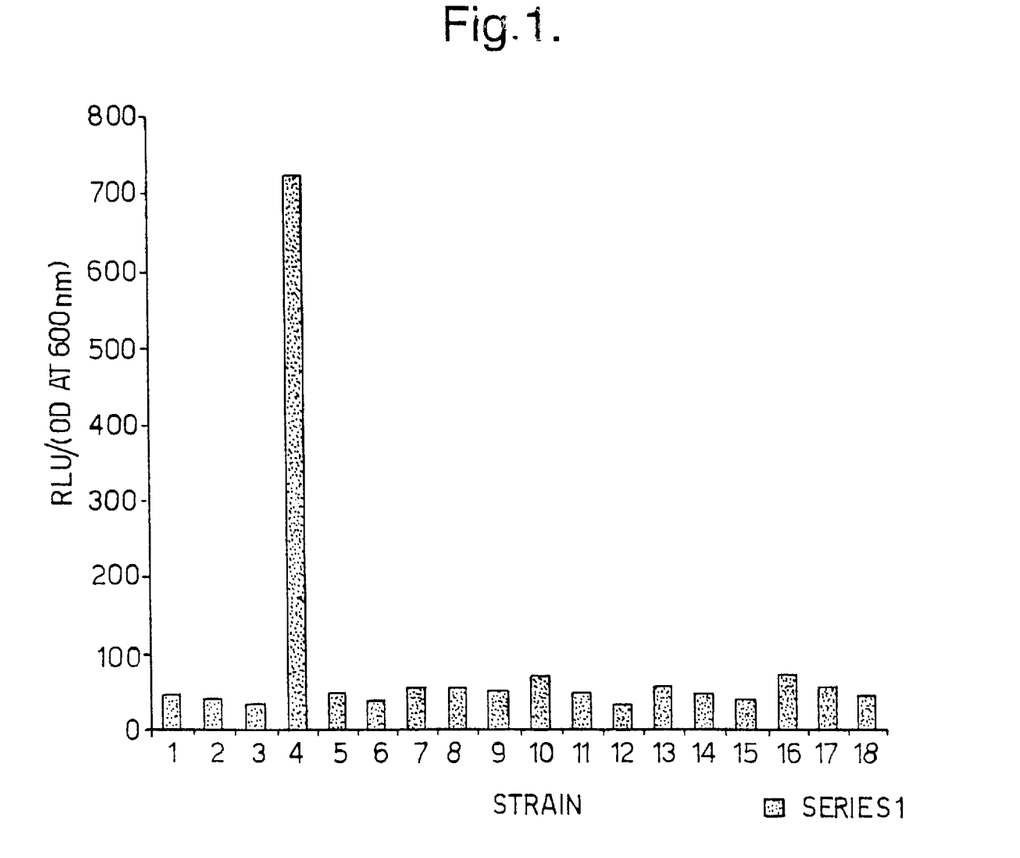
FIG. 1 shows the results of a luciferase assay performed on diploid yeast following a two hybrid assay.

The diploids were grown up on selective media and the luciferase activity assayed as follows: 1.5 ml of culture was pelleted by spinning for 2 minutes in a microfuge. The cells were resuspended in 100 μl of citrate buffer pH 2.7. In a Berthold Lumat luminometer 100 μl of 0.56 mg/ml luciferin (USB, Cleveland, Ohio) solution in 25 mM Tris-phosphate pH 7.75 was injected and the highest count of relative light units (RLU) reached over 2 minutes was recorded. The results of luciferase assay are shown in FIG. 1 (results are the mean of three independent experiments).

Significantly higher amounts of luciferase activity were detected in strain 4, which contains the cJun and ATF2 hybrid proteins, compared to the control strains 5 and 6 which express cJun and Lamin C hybrid proteins or cJun hybrid protein and Gal4p activation domain respectively. This observation leads to the suggestion that the ATF2/cJun is a genuine interaction. In contrast there was no significant increase in luciferase activity found in the test strains 7, 10, 13 and 16, compared to their respective controls (strains 8, 9; 11, 12; 14, 15; 17, 18). This data indicates that these strains are false positives. However, it has been found that some bait hybrid proteins are functional in a 2-hybrid assay as a LexA fusion, but not as a Gal4 DNA binding domain fusion (21). So therefore it can be concluded that cJun does interact with ATF2, and that the polyA, BS69, FP#2 and FP#3 proteins are unlikely to do so. This is consistent with the result previously obtained that cJun interacts with ATF2 (22).

There was no significant luciferase activity detected jn the control diploids containing the Lamin C or empty bait (pDM61). This data indicates that, in this case, the false positive activation to produce the first signal (the expression of His3p) produced by false activation of reporter gene expression was due to the binding of the second hybrid protein to the lexAo.

REFERENCES

1. Fields, S. and Song, O.-K. (1989) *Nature* 340: 245–246.
2. Wilson, T. E., Padgett, K. A., Johnson, M. and Milbrandt, J. (1993) *Proc. Natl. Acad. Sci. USA* 90: 9186–9190.
3. Bartel, P., Chien, C.-T., Sternglanz, R. and Fields, S. (1993) *Biotechniques* 14: 920–924.
4. Harper, J. W., Adami, G. R., Wei, N., Keyomarsi, K. and Elledge, S. J., (1993) *Cell* 75: 805–816.
5. Alien, T. B., Walberg, M. W., Edwards, M. C. and Elledge, S. J. (1995) *TIBS* 20: 511–516.
6. Harper, J. W. et al (1993) *Cell* 75: 805–816.
7. Le Douarin, B. et al (1995) *Nucl. Acids. Res.* 23: 876–878.
8. Johnsson, N. and Varshavsky, A. (1994) *Proc. Natl. Acad. Sci. USA*. 91:10340–10344.
9. Gyuris, J., Golemis, E., Chertkov, H., and Brent, R. (1993) *Cell* 75: 791–803.
10. Dalton, S. and Treisman, R. (1992) *Cell* 68: 597–612.
11. Yang, M., Wu, Z. and Fields, S. (1995) *Nucl. Acids Res.* 23:1152–1156.
12. Sambrook, J., Fritsch, E. F. and Maniatis, T. (1989) Molecular Cloning ed Cold Spring Harbor Laboratory Press.
13. Sherman, F. (1991) Guide to yeast genetics and molecular biology. Methods in Enzymology 194 3–21.
14. Gietz D., St Jean, A., Woods, R. A. and Schiestl, R. H. (1992) Nucleic Acids Res. 20 1425.
15. Boeke, J. D., LaCroute, F. and Fink, G. R. (1984) Mol. Gen. Genet. 197 345–346.
16. Jayaraman P.-S., Hirst, K. and Goding, C. R. (1994) EMBO 13 2192–99.
17. Sikorski, R. S. and Hieter, P. (1989) Genetics 122 19–27.
18. Brent, R. and Ptashne, M. S. (1989) U.S. Pat. No. 4,833,080.
19. Stotz, A. and Linder, P. (1990) Gene 95 91–98.
20. Feilotter, H. H. et al (1994) Nucleic Acids Res. 22 1502–3.
21. Hong, Y.-R., Han, L., Huang, J. and Kleinberg, M. E. (1996) Kaohsiung J Med Sci 12 301–305.
22. Du, W., Thanos, D. and Maniatis, T. (1993) Cell 74 887–898.
23. Norman, C., Runswick, M., Pollock, R. and Treoman, R. (1988) Cell 55: 989–1003.
24. Liv, F. and Green, M. R. (1990) Cell 61: 1217–1224.

We claim:

1. A method for detecting an interaction between a first test protein and a second test protein, which method comprises:

a) providing a host cell;

b) providing a first chimeric gene that is capable of being expressed in the host cell, the first chimeric gene comprising a DNA sequence that encodes a first hybrid protein, the first hybrid protein comprising:
  (i) a first test protein that is to he tested for interaction with a second test protein; and
  (ii) a first detection domain;

c) providing a second chimeric gene that is capable of being expressed in the host cell, the second chimeric gene comprising a DNA sequence that encodes a second hybrid protein, the second hybrid protein comprising:
  (i) a second test protein that is to be tested for interaction with the first test protein; and
  (ii) a second detection domain;

d) providing a control chimeric gene that is capable of being expressed in the host cell, the control chimeric gene comprising a DNA sequence that encodes a control hybrid protein, the control hybrid protein comprising:

(i) the first test protein; and (ii) a control detection domain;

wherein when the first detection domain and the second detection domain are brought into proximity to one another by an interaction between the first and second hybrid proteins, a first detectable signal is produced, and when the second detection domain and the control detection domain are brought into proximity to one another by an interaction between the second hybrid protein and the control hybrid protein a second detectable signal is produced which is distinguishable from the first detectable signal;

e) introducing the first chimneric gene and the second chimeric gene into the host cell and subjecting the host cell to conditions under which the first and second hybrid proteins are expressed in sufficient quantity for the first detectable signal to be produced;

f) introducing the control chimeric gene into the host cell in the presence of the first and second chimeric genes and subjecting the host cell to conditions under which the control hybrid protein is expressed in sufficient quantity for the second detectable signal to be produced;

g) determining whether either or both of the detectable signals are produced, thereby identifying the status of the interaction between the first test protein and the second test protein as true positive or false positive, wherein there is further provided in the host cell, a first reporter gene which is activated to produce the first detectable signal when the first and second hybrid proteins interact, and a second reporter which is activated to produce the second detectable signal when the second and control hybrid proteins interact;

wherein said method is a modified two-hybrid assay in which the first detection domain comprises a first DNA-binding domain which recognises a DNA binding site on the first reporter gene; the second detection domain comprises a transcription activation domain; the control detection domain comprises a second DNA-binding domain which recognises a DNA binding site on the second reporter gene; the reporter genes are activated by the transcription activation domain when this is in sufficient proximity to the reporter genes; and the DNA binding sites on the reporter genes are different.

2. A method as claimed in claim 1, wherein the first and second reporter genes have different promoters.

3. A method as claimed in claim 1, wherein the first hybrid protein and the control hybrid protein have no protein binding sites in common other than protein binding sites specific to the first test protein.

4. A method as claimed in claim 1, for screening proteins encoded by a DNA library, wherein the second test protein is encoded by a DNA sequence from a cDNA library.

5. A method as claimed in claim 1, wherein step f) is performed by mating haploid yeast cells of opposite mating type, one containing the first reporter gene and chimeric genes encoding the first and second hybrid proteins and another containing the second reporter gene and a chimeric gene encoding the control hybrid protein.

6. A method as claimed in claim 1, wherein the first hybrid protein and the control hybrid protein are in the form of a single dual hybrid protein, comprising the first test protein and the two different DNA-binding domains.

7. A method as claimed in claim 4, wherein the host cell is yeast.

8. A method as claimed in claim 6, wherein the first and second test proteins are derived from cDNA libraries.

9. A method as claimed in claim 6, wherein step f) is performed by mating haploid yeast cells of opposite mating type, one containing a chimeric gene encoding the dual hybrid protein and the first and second reporter genes and another containing a chimeric gene encoding the second hybrid protein.

10. A method of performing a two-hybrid assay in yeast, which method comprises mating two yeast cells of opposite mating type, the yeast cells respectively comprising (i) a first chimeric gene encoding a hybrid protein comprising a first DNA-binding domain and a first test protein, a second chimeric gene encoding a hybrid protein comprising a transcriptional activation domain and a second test protein, and a first reporter gene having a DNA binding site recognised by the first DNA-binding domain; and (ii) a third chimeric gene encoding a hybrid protein comprising a second DNA-binding domain and a third test protein, and a second reporter gene having a DNA binding site recognised by the second DNA-binding domain, the first and second DNA-binding domains and DNA binding sites being different; and determining whether the reporter genes are expressed.

11. A kit for detecting an interaction between pairs of test proteins, which kit comprises:

(a) two different bait vectors capable of expressing two different hybrid proteins comprising different DNA-binding domains and a first test protein, each vector comprising a nucleic acid sequence which encodes one of the DNA-binding domains and an insertion site for a nucleic acid sequence encoding the first test protein; or (b) a single bait vector capable of expressing a dual bait hybrid protein comprising two different DNA-binding domains and a first test protein, the vector comprising nucleic acid sequences which encode the DNA-binding domains and an insertion site for a nucleic acid sequence encoding the first test protein; and (c) an activator vector capable of expressing an activator hybrid protein comprising a transcriptional activation domain and a second test protein, the vector comprising a nucleic acid sequence which encodes the activation domain and an insertion site for a nucleic acid sequence encoding the second test protein; and (d) two reporter genes capable of producing different detectable signals, each reporter gene having a DNA binding site for one of the DNA-binding domains encoded by the bait vector or vectors.

* * * * *